United States Patent
Kim (10) Patent No.: US 7,495,757 B2
(45) Date of Patent: Feb. 24, 2009

(54) SEMICONDUCTOR MANUFACTURING APPARATUS AND WAFER PROCESSING METHOD

(75) Inventor: Seok-Bae Kim, Gyeonggi-do (KR)

(73) Assignee: Samsung Electronics Co., Ltd., Suwon-si, Gyeonggi-do (KR)

( * ) Notice: Subject to any disclaimer, the term of this patent is extended or adjusted under 35 U.S.C. 154(b) by 35 days.

(21) Appl. No.: 11/426,549

(22) Filed: Jun. 26, 2006

(65) Prior Publication Data

US 2006/0292714 A1 Dec. 28, 2006

(30) Foreign Application Priority Data

Jun. 24, 2005 (KR) .................. 10-2005-0055230

(51) Int. Cl.
*G01N 21/00* (2006.01)
(52) U.S. Cl. .................. 356/237.1; 356/237.2
(58) Field of Classification Search .......... None
See application file for complete search history.

(56) References Cited

U.S. PATENT DOCUMENTS

| | | | | |
|---|---|---|---|---|
| 4,907,035 | A * | 3/1990 | Galburt et al. | 356/150 |
| 5,420,663 | A * | 5/1995 | Nakajima et al. | 355/50 |
| 6,943,364 | B2 * | 9/2005 | An | 250/559.42 |
| 2005/0237529 | A1 * | 10/2005 | Kanno et al. | 356/426 |
| 2005/0280807 | A1 * | 12/2005 | Backhauss et al. | 356/237.2 |

FOREIGN PATENT DOCUMENTS

| | | |
|---|---|---|
| JP | 2004-179211 | 6/2004 |
| KR | 2002-0061994 | 7/2002 |
| KR | 10-2003-54243 | 7/2003 |
| KR | 2003-0057548 | 7/2003 |
| KR | 10-2004-48599 | 6/2004 |
| KR | 10-2004-0077287 | 9/2004 |

OTHER PUBLICATIONS

English language abstract of Korean Publication No. 10-2003-54243.
English language abstract of Korean Publication No. 10-2004-48599.
English language abstract of Japanese Publication No. 2004-179211.

* cited by examiner

*Primary Examiner*—Michael P Stafira
(74) *Attorney, Agent, or Firm*—Marger Johnson & McCollom, P.C.

(57) ABSTRACT

A semiconductor manufacturing apparatus and a wafer processing method are disclosed. The semiconductor manufacturing apparatus, comprises a rotatable device for supporting a wafer. A sensor for irradiating a laser beam onto a surface of the wafer and a detector including a plurality of modules for detecting the laser beam reflected from the wafer are also included. The sensor obtains information regarding the wafer, based on a change in the surface status of the wafer, which the modules sense when the laser beam is reflected from the wafer.

12 Claims, 12 Drawing Sheets

SEMICONDUCTOR MANUFACTURING APPARATUS AND WAFER PROCESSING METHOD

CLAIM FOR PRIORITY

This application is based on and claims priority to Korean Patent Application No. 2005-55230 filed on Jun. 24, 2005 in the Korean Intellectual Property Office (KIPO), the entire contents of which are hereby incorporated by reference.

BACKGROUND

1. Field of the Invention

The present invention relates in general to the field of a semiconductor manufacturing apparatus and a wafer processing method. More particularly, it relates to a semiconductor manufacturing apparatus and a wafer processing method that can detect a process error and perform feedback regarding the wafer.

2. Description of the Related Art

In order to manufacture a semiconductor device, various patterns such as wiring, a transistor and a capacitor are generally formed on a silicon wafer. For the purpose of forming these patterns, a photolithography process of depositing a thin film on a wafer, form a photoresist pattern on the thin film and then etching the thin film according to the photoresist pattern is usually used. The photolithography is the process of coating a photoresist onto the wafer on which the thin film is deposited, illuminating a light onto the photoresist, developing a photoresist pattern reacted to the light, and forming a specific photoresist pattern by selectively removing the photoresist. The photoresist pattern, which is formed through the photolithography process, is used as an etching mask in an etching process.

A series of inspection process is performed for inspecting the photoresist pattern formed through the photolithography process prior to the etching process. These inspection processes include a defect inspection of the photoresist pattern, an edge bead removal (EBR) inspection for removing the photoresist on an edge of the wafer, an EBR size inspection, reticule error inspection, and others. After advancing a photoresist coating process and the following processes, a worker performs monitoring of the EBR size in order to check whether the EBR size is within a set range. In other words, if a poor EBR size is detected after all processes, checking and verifying the irregular EBR size is performed too late, thereby increasing time loss and damage accordingly. Additionally, checking and verifying the EBR size has been limited to accurately perform monitoring, since it depends significantly on a level of skill of an operator. Further, it has caused problems of loss of equipment and quality deterioration of the previously advancing wafer, because proper processing was not performed up until a centering error of the wafer related to the poor EBR size was detected.

SUMMARY

An object of the present invention is to provide a semiconductor manufacturing apparatus and a wafer processing method, which can exactly detect and verify whether an EBR size is irregular and whether there is a centering error on a wafer.

Another object of the present invention is to provide a semiconductor manufacturing apparatus and a wafer processing method, which can correct the centering of a wafer using light and measure an EBR size accurately and reliably.

According to an aspect of the present invention, there is provided a semiconductor manufacturing apparatus, comprising a rotatable device for supporting a wafer. Furthermore, there is a sensor for irradiating a laser beam onto a surface of the wafer. Also, a detector including a plurality of modules for detecting the laser beam reflected from the wafer. The sensor obtains information regarding the wafer, based on a change in the surface status of the wafer which the modules sense when the laser beam is reflected from the wafer. In one embodiment, the sensor includes a projector. In a further embodiment, the rotatable device for supporting a wafer comprises a rotatable chuck.

The information regarding the wafer preferably includes at least one of (a) the centering status of the wafer as supported on the rotatable device, and (b) the edge bead removal size of the wafer. In another embodiment, the laser beam irradiated from the sensor crosses an upper surface of the wafer. In a further embodiment, the sensor irradiates the laser beam on an edge of the rotating wafer.

In another further embodiment, the semiconductor manufacturing apparatus, can comprise a rotatable device for supporting a wafer having a photoresist coated thereon. It can also include a nozzle for spraying chemicals for removing the photoresist coated on an edge of the wafer, a sensor for irradiating a laser beam on the edge of the wafer, and a detector for detecting the laser beam reflected from the wafer, configured to obtain a waveform of a surface status of the wafer. The sensor can measure the width of the wafer edge from which the photoresist is removed by the chemicals and senses at least one of the eccentricity of the wafer and the width of the wafer edge from which the photoresist is removed. In another embodiment, the manufacturing apparatus can comprise a wafer centering device including a light emitter located on an upper part of the wafer edge and a light receiver on a lower part of the wafer edge. The wafer centering device can be configured to detect the wafer centering based on whether the light receiver senses light.

A wafer processing method can also be provided. The method can comprise providing a wafer, coating a predetermined material on the wafer removing the predetermined coating material from an edge of the wafer, irradiating a laser beam onto the wafer edge from which the predetermined material is removed, obtaining information on a predetermined position of the wafer based on a sensing position of the laser beam reflected from the wafer edge, and correcting the position of the wafer, if the information indicates that the wafer is not in the predetermined position. In one embodiment, the step of irradiating the laser beam on the wafer edge from which the predetermined material is removed and obtaining the information on the position of the wafer according to the sensing position of the laser beam reflected from the wafer edge comprises irradiating a laser beam crossing the upper part of the wafer. In another embodiment, the step of irradiating the laser beam on the wafer edge from which the predetermined material is removed and obtaining the information on the position of the wafer according to the sensing position of the laser beam reflected from the wafer edge comprises rotating the wafer and irradiating the laser beam on an edge of the rotating wafer. In a still another embodiment, the step of irradiating the laser beam on the wafer edge, from which the predetermined material is removed, and obtaining the information on the position of the wafer according to the sensing position of the laser beam reflected from the wafer edge further comprises measuring the width of the wafer edge from which the predetermined material is removed.

The present invention may advance the monitoring of the EBR size following conducting an EBR process. It may also automatically control the EBR size or the wafer centering using a feedback system, in case the EBR size is poor, thereby improving the reliability of measuring the EBR size and the quality of the wafer.

The present invention will not be limited to the technical objects described above. Other objects not described herein will be more definitely understood by those skilled in the art from the following detailed description.

BRIEF DESCRIPTION OF THE DRAWINGS

Example embodiments of the present invention will become more apparent by describing in detail example embodiments of the present invention with reference to the accompanying drawings, in which.

DETAILED DESCRIPTION OF EXEMPLARY EMBODIMENTS

Subject matters and features of the exemplary embodiments of the present invention will be covered by the detailed description and drawings.

Advantages and features of the present invention and methods of accomplishing the same may be understood more readily by reference to the following detailed description of the exemplary embodiments and the accompanying drawing. The present invention may, however, be embodied in many different forms and should not be construed as being limited to the exemplary embodiments set forth herein. Rather, these exemplary embodiments are provided so that this disclosure will be thorough and complete and will fully convey the concept of the invention to those skilled in the art, and the present invention will only be defined by the appended claims. Like reference numerals refer to like elements throughout the specification.

Exemplary embodiments of the present invention will be described in more detail with reference to the accompanying drawing.

Hereinafter, preferred embodiments of the present invention will be described in detail with reference to the accompanying drawing. The embodiments will be explained in detail for enabling those skilled in the art to execute the present invention.

Figure 1:
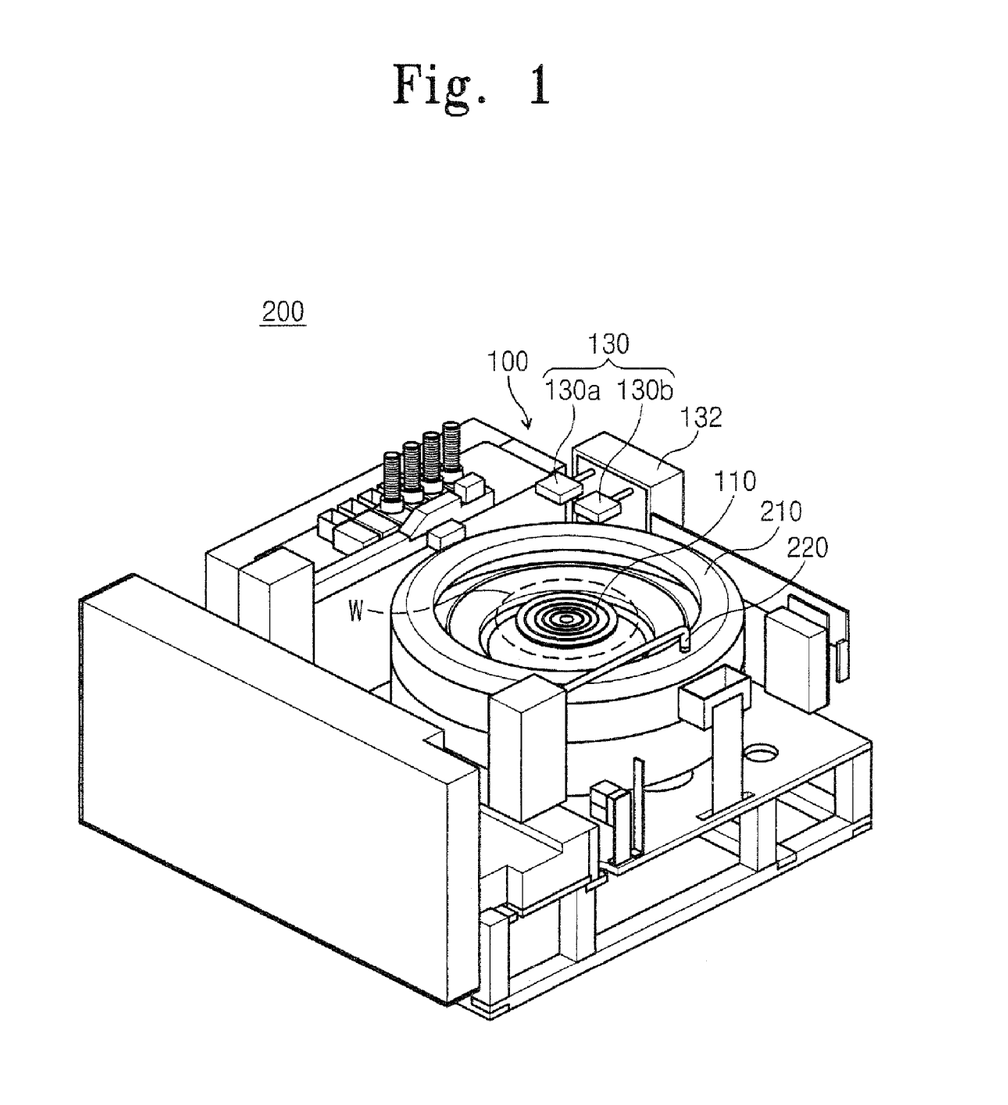
FIG. 1 is a perspective view illustrating a semiconductor manufacturing apparatus according to an exemplary embodiment of the present invention.

Referring to FIG. 1, a semiconductor manufacturing apparatus 200 is an example of a coating process unit for coating a photoresist on a wafer and removing the photoresist formed irregularly on an edge of the wafer, namely an edge bead. The apparatus 200 is provided with a spin chuck 110 for supporting the wafer (W) using a vacuum absorption method or other suitable methods, and a bowl 210 arranged around the spin chuck 110 for preventing the dispersion of the photoresist and the rinse liquid. Additionally, an EBR nozzle 220 for removing the edge bead formed on the edge of the wafer is provided.

Figure 2:
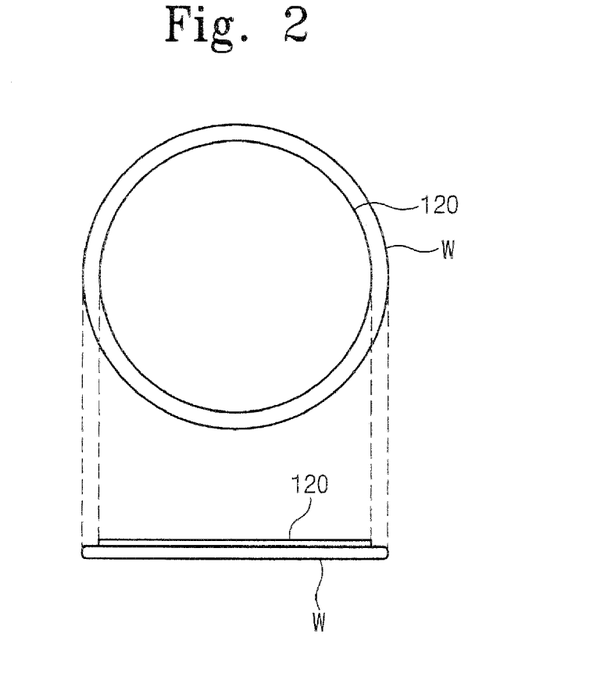
FIGS. 2 and 3 are respectively a plan and a front view illustrating an EBR result using the semiconductor manufacturing apparatus according to the exemplary embodiment of the present invention.
Figure 3:
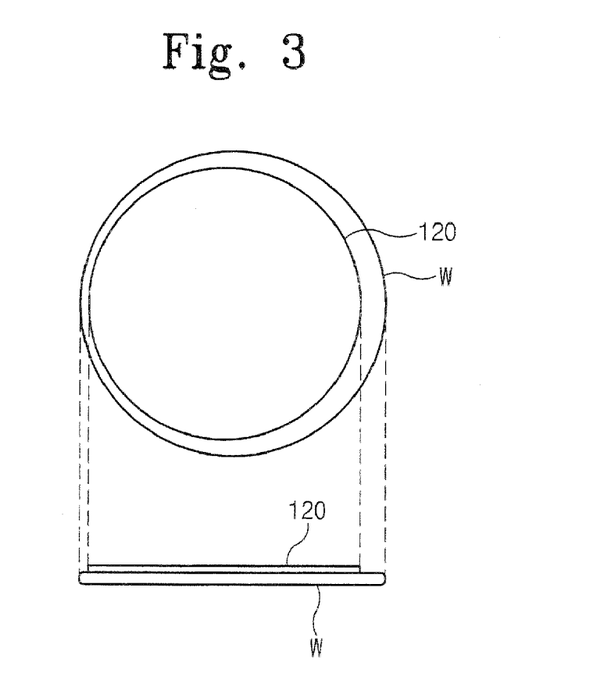

If a photoresist 120 is coated on the wafer (W), the rinse liquid such as a thinner is discharged from the nozzle 220 to the edge of the rotating wafer (W) in order to remove the edge bead. As shown in FIG. 2, an EBR size becomes uniform, covering the edge of the wafer, if the wafer centering is accurately adjusted. However, as shown in FIG. 3, the EBR size becomes non-uniform, if the wafer centering is poor. In other words, since the photoresist 120 is excessively removed from one edge of the wafer and incompletely removed from the other, the EBR size becomes non-uniform.

Accordingly, the semiconductor manufacturing apparatus 200 includes a sensing unit 100 having a sensor 130 configured to detect (a) whether the wafer is eccentric and (b) the EBR size. The sensor 130 comprises a projector 130a for illuminating a laser beam and a detector 130b for sensing the laser reflected from the wafer (W). The projector 130a and the detector 130b are controlled by a control unit 132.

Figure 4:
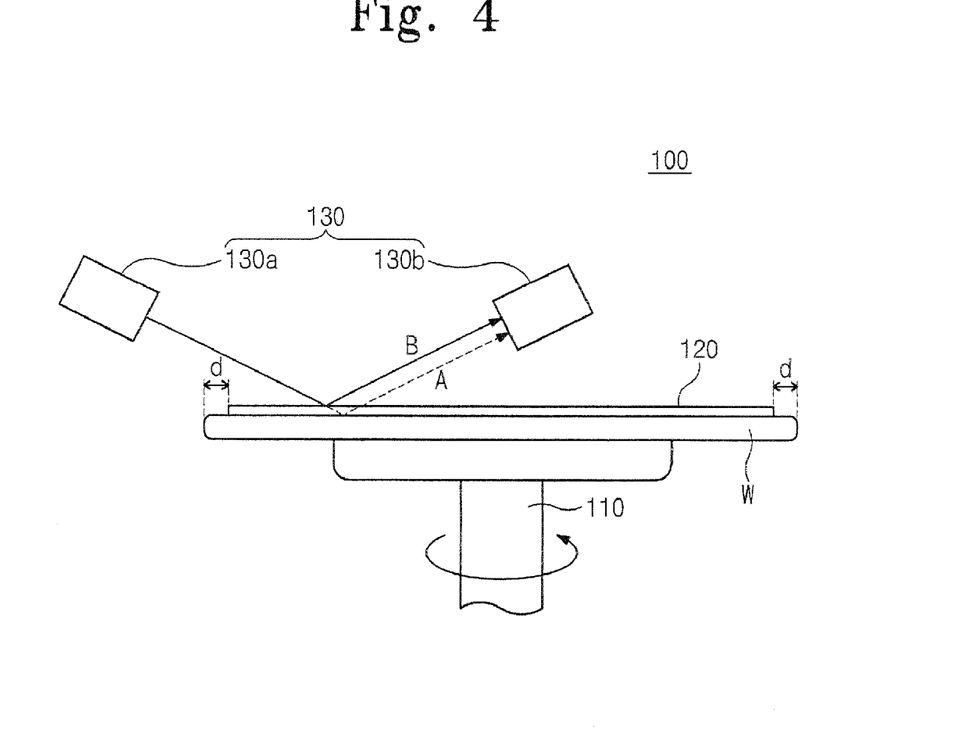
FIG. 4 is a cross-sectional view describing a sensing operation of a sensor in the semiconductor manufacturing apparatus according to the exemplary embodiment of the present invention.

Referring to FIG. 4, the projector 130a illuminates a laser onto the wafer (W) which has passed through the EBR process and senses the laser reflected from the detector 130b. At this time, the laser illuminated onto a part of which the photoresist 120 is removed from surface of the wafer (W) enters into the detector 130b through a light path A. However, the laser illuminated onto a part of which the photoresist 120 is not removed from the wafer enters into the detector 130b through a light path B. In other words, a reflection path of the laser becomes different according to whether the photoresist 120 is in existence. Additionally, as the spin chuck 110 is rotating, the sensing operation is performed on the whole edge of the wafer (W).

Figure 5:
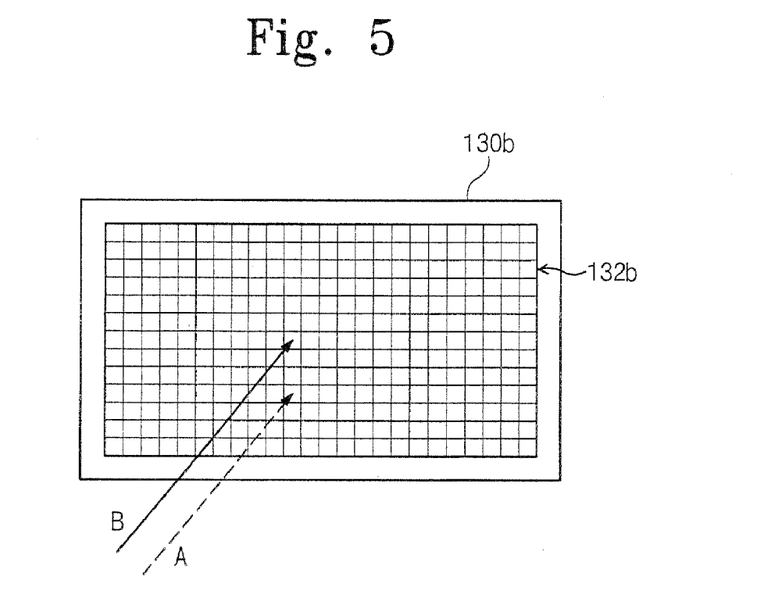
FIG. 5 is a front view illustrating a part of a detector in the semiconductor manufacturing apparatus according to the exemplary embodiment of the present invention.

Referring to FIG. 5, a plurality of pixels 132b are arrayed in the detector 130b. Accordingly, the pixels 132b sense respectively the laser entering through the light path A and B. Thus, one of the pixels 132b senses the laser reflected from the part of which the photoresist 120 is removed from the wafer and another one of the pixels 132b senses the laser reflected from the part of which the photoresist 120 is formed. The detector 130b can judge whether the photoresist 120 is removed, based on information on the sensed laser. However, when the laser is continuously illuminated onto the rotating wafer (W), if the laser reflected from the wafer is detected at different location by the detector 130b, it means that the EBR size is different, i.e., the wafer centering is poor.

Figure 6:
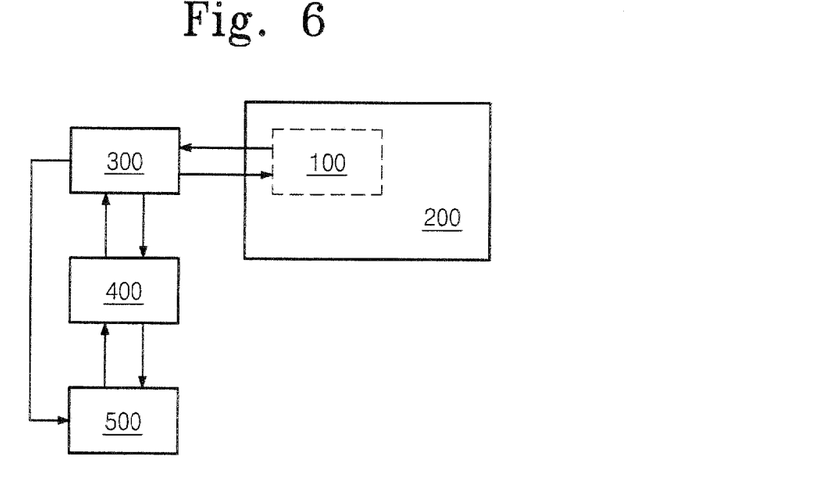
FIG. 6 is a configuration view of the semiconductor manufacturing apparatus according to an exemplary embodiment of the present invention.

Referring to FIG. 6, the semiconductor manufacturing apparatus 200 including the sensing unit 100 is controlled by a main controller 500. The main controller 500 communicates with a machine controller 400, and the machine controller 400 communicates with an input/output board (I/O board) 300 of the sensor 100. The main controller 500, as an equipment controller, has main functions of main machine interface and data management, for example, process status, equipment status, recipe management and the like. The machine controller 400 has main functions of controlling, monitoring and collecting all sorts of data of system hardware including a robot arm and a nozzle.

Figure 7:
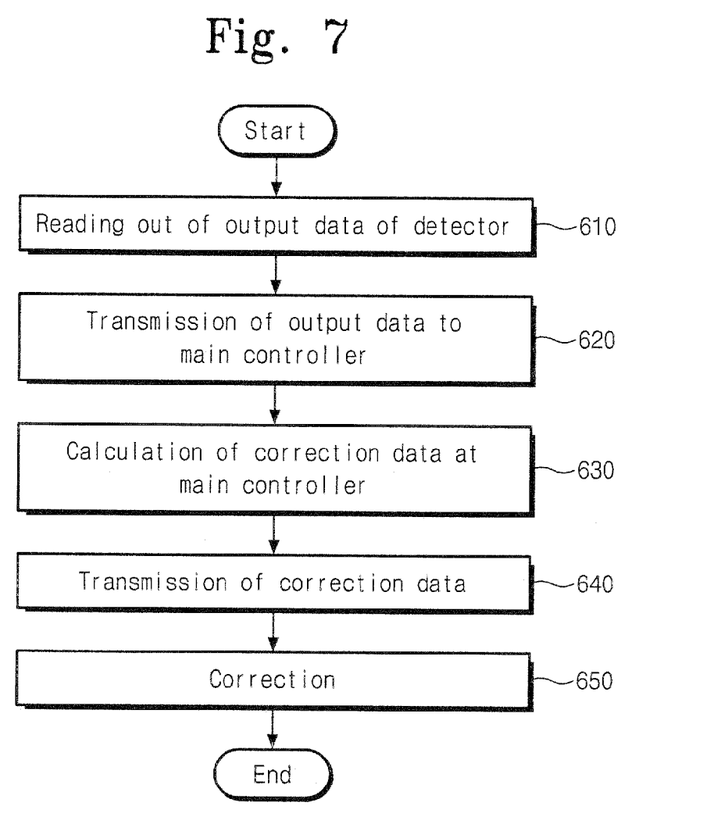
FIG. 7 is a flow chart illustrating a wafer centering correction process in the semiconductor manufacturing apparatus according to an exemplary embodiment of the present invention.

Referring to FIG. 7, when it is confirmed that the wafer centering is poor (step 610), due to the sensing operation of the sensor 100, this information is sent to the main controller 500 through a sensor I/O board 300 (step 620). The main controller 500 calculates correction data about the wafer centering on the basis of this information (step 630), and then transmits the data to the machine controller 400 which controls the robot and (step 640). The robot arm makes it possible to correct the wafer centering on the basis of the corrected data, when the wafer is loaded (step 650). The following processes can be conducted after the wafer centering. Though only the wafer centering is explained, it is possible to be applied to other information such as the EBR size as described below including the wafer centering.

Referring again to FIG. 4, the sensor 130 may measure an EBR size (d). Therefore, in the case where the protector 130a illuminates the laser moving from the edge of the wafer (W) toward a central axis of the wafer (W) and the detector 130b detects the laser, when a position of the laser detected by the detector 130b is changed, the changed position corresponds to a part of which the photoresist 120 is coated. Accordingly, the EBR size (d) is from a circumference of the wafer to a part from which the waveform of the laser detected by the detector 130b to is changed. If the EBR size is within a predetermined range, the following processes are advanced. If not so, the following processes are not advanced by setting an interlock, and the EBR size (d) is set within the predetermined range by resetting a position of the EBR nozzle 220.

Figure 8:
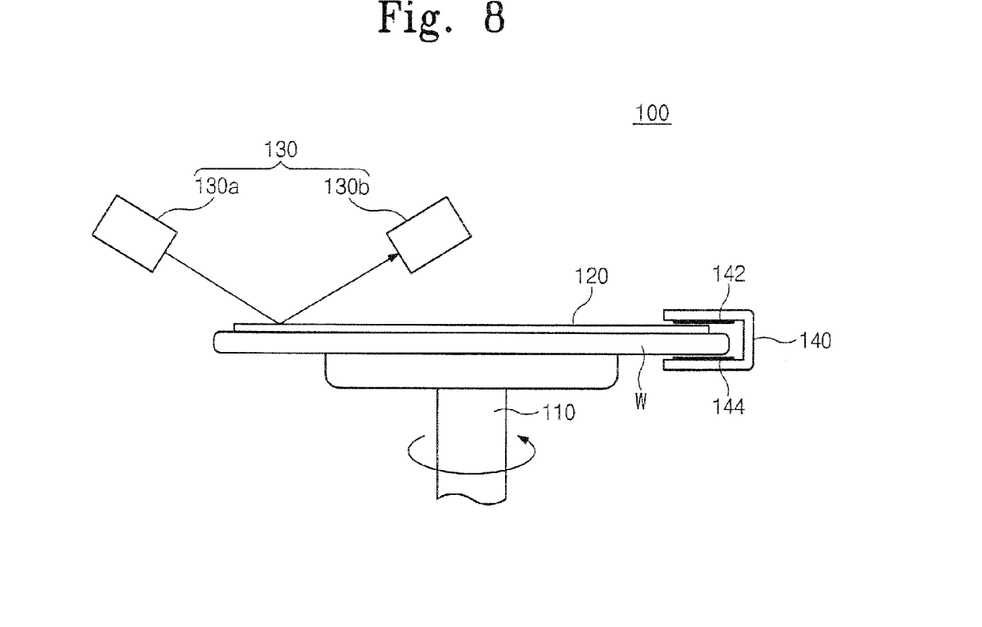
FIG. 8 is a cross-sectional view illustrating a sensor in the semiconductor manufacturing apparatus according to another exemplary embodiment of the present invention.

Referring to FIG. 8, a sensor 140 may include a light emitter 142 and a light receiver 144, in order to accurately correct the wafer centering. The light emitter 142 and the light receiver 144 may be respectively composed of a charged couple display (CCD) that includes a plurality of pixels. The CCD light receiver 144 detects light generated from respective pixels of the CCD light emitter 142 by each pixel, and the light which is not detected from pixels that is located in a part shielded by the wafer (W). Accordingly, the CCD light receiver 144 determines whether the wafer centering is proper, according to whether the light is detected from respective pixels.

Figure 9:
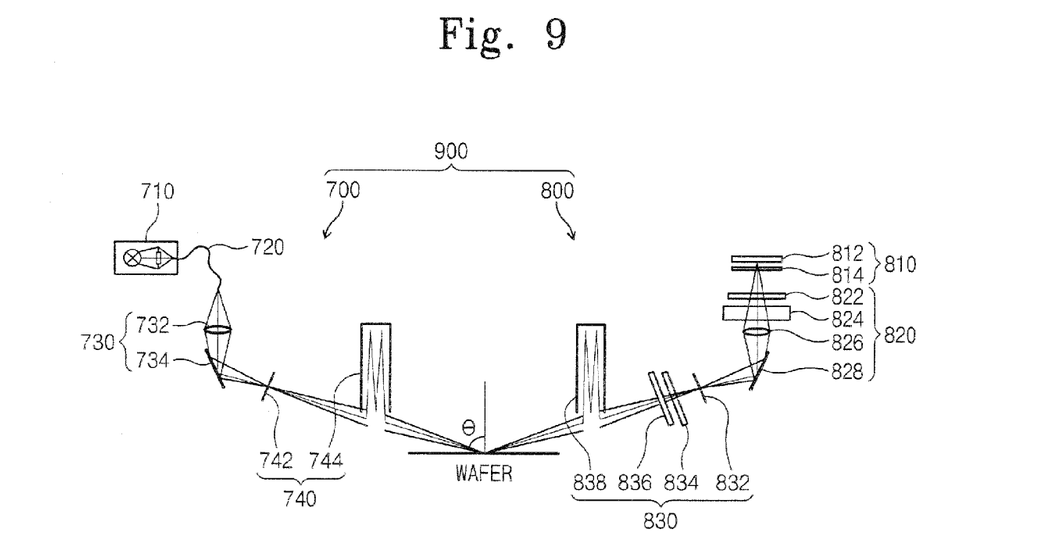
FIG. 9 shows a configuration view illustrating a sensing unit in the semiconductor manufacturing apparatus according to still another exemplary embodiment of the present invention.

Referring to FIG. 9, a sensing unit 900 includes a projector 700 for irradiating a laser and a detector 800 for sensing the laser and detecting the high and low emissions of an illuminated object. The projector 700 includes a lamp 710 as a light source of the laser, an optical cable 720 for providing a path to the laser generated from the lamp 710, an illumination unit 730 having a lens 732 and a mirror 734, and a projection unit 740 composed of a projection grating unit 742 and a window 744. The detector 800 includes a detection unit 830, a modulation unit 820 and a data acquisition module (DAM) 810. The detection unit 830 comprises a window 838 onto which the laser reflected from the wafer (W) enters, a polarizing lens 836, a birefringent plate 834 and a detection grating unit 832. The modulation unit 820 comprises a mirror 828, a lens 826, an optical modulator 824 and a polarizing lens 822. The data acquisition module (DAM) 810 comprises a lens array 814 and a sensor 812.

Figure 10:
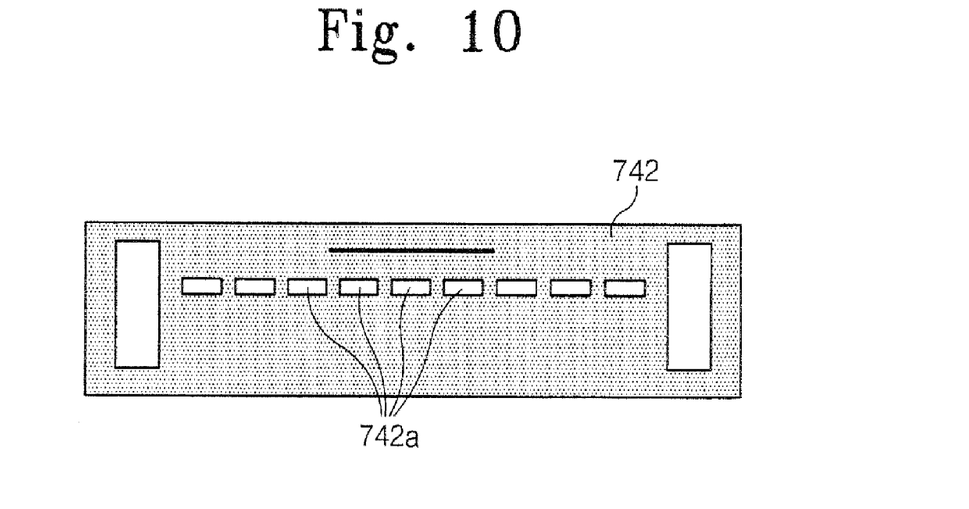
FIGS. 10 and 11 are front views respectively illustrating projection grating and detection grating according to an exemplary embodiment of the present invention.
Figure 11:
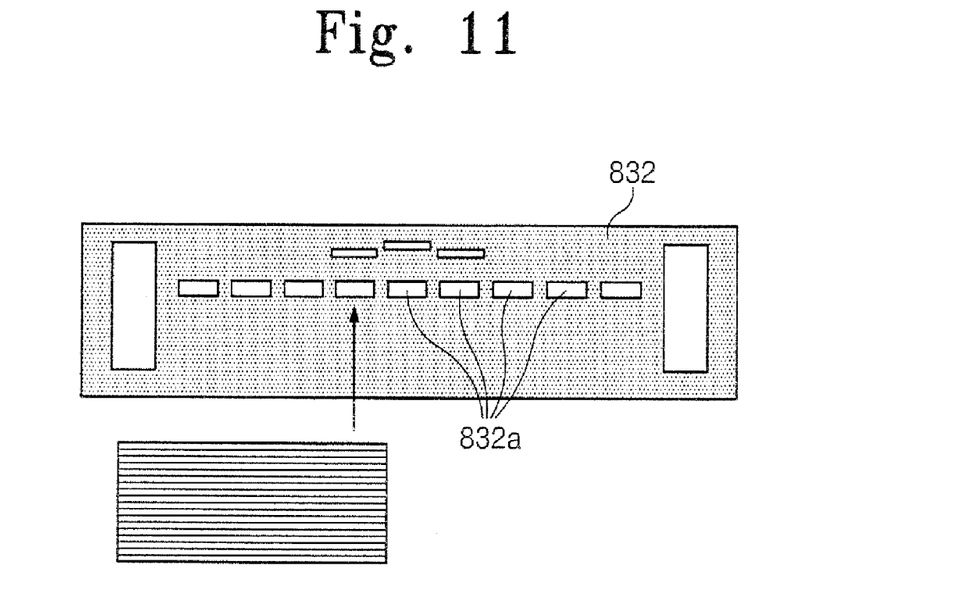

Referring to FIGS. 10 and 11, the projection grating unit 742 and the detection grating unit 832 are respectively composed of a plurality of cells or gratings 742a and 832a. A ruler is engraved on the gratings 742a and 832a respectively. For example, the grating 742a and 832a can be respectively arranged at the width of about 2.80 mm, the height of 2.50 mm and the pitch of 3.40 mm. The gratings 742a and 832a having these configurations make it possible to more accurately measure a search area, though still limited, in comparison with a capture system of taking charge of wide areas.

Referring again to FIG. 9, the laser beam generated from the lamp 710 enters into the projection grating unit 742 by passing through an illumination unit 730 via the optical cable 720. The laser beam which passes through the projection grating unit 742 is converted to a slit shape and reflected onto the wafer (W). The laser beam reflected onto the wafer (W) passes through a polarizing lens 836. A projection grating image reflected from the polarizing lens 836 is polarized and projected onto the birefringent plate 834. The birefringent plate 834 divides the incident laser beam into two components. One of these components is an ordinary beam and the other is an extraordinary beam. These beams are crossed each other at an angle of 90 degrees.

The two components are projected onto the detection grating unit 832 and the laser beam passes through the detection grating unit 832 where it is detected by the DAM 810. The DAM 810 includes a series of light-sensing diodes.

Figure 12:
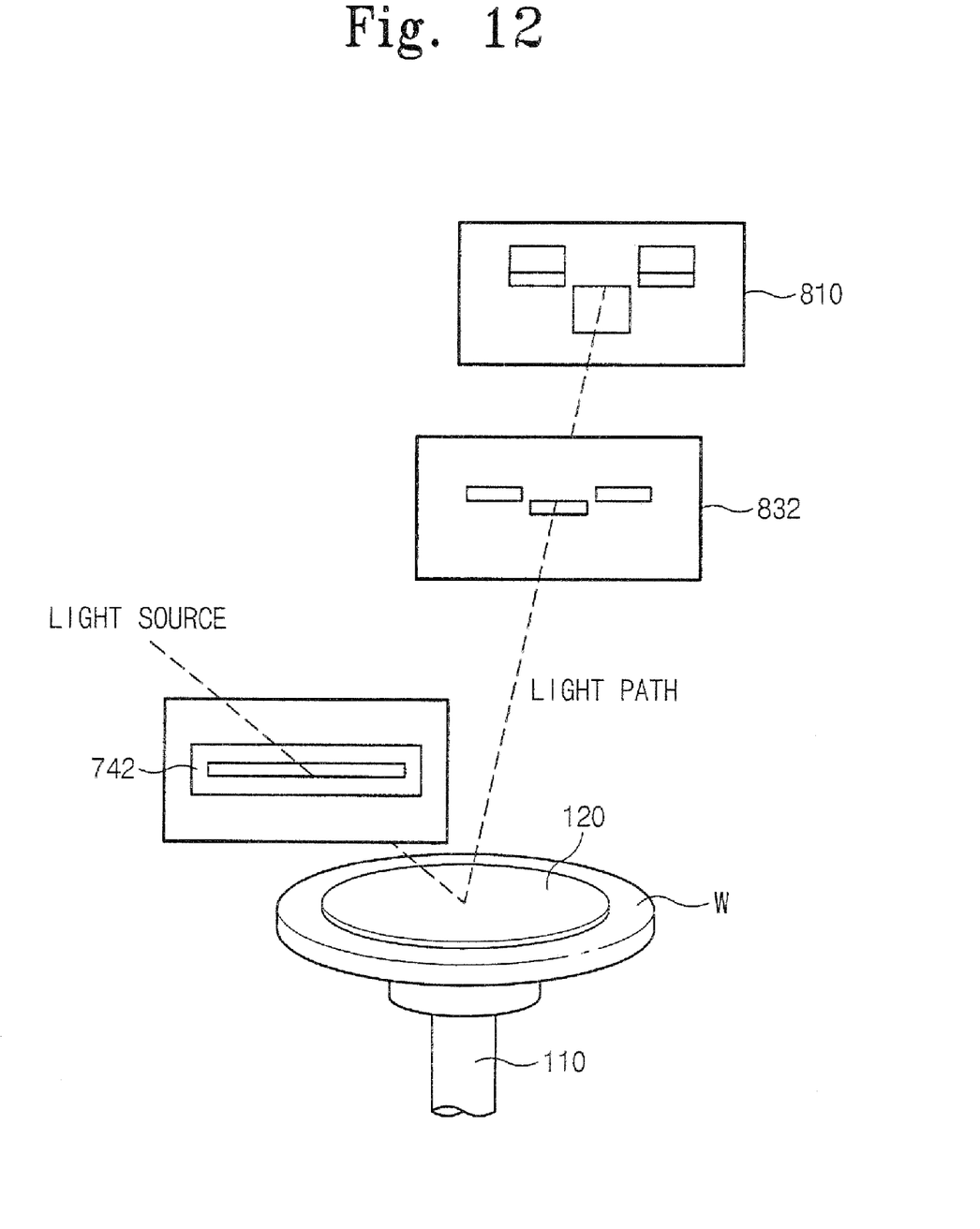
FIG. 12 is a configuration view explaining a sensing operation of the sensor according to an exemplary embodiment of the present invention.

Referring to FIG. 12, when the wafer (W) is located on a high location, if the beam is illuminated to the photoresist 120 on the wafer (W), output values of cells on both sides among three cells of the detection grating unit 832 are higher than that of a cell in the middle. This means that the photoresist 120 is existed on the wafer (W). In other words, if the wafer centering is poor, it indicates what direction the chuck 110 for supporting the wafer (W) is moved. Thus, the wafer centering is corrected by information sensed by the sensing unit 900 of FIG. 9. Additionally, it may be also useful to control the height of the chuck 110. In other words, the height of the chuck 110 is controlled until there is no a signal output difference among three cells in the detection grating unit 832 using the sensing unit 900.

Figure 13:
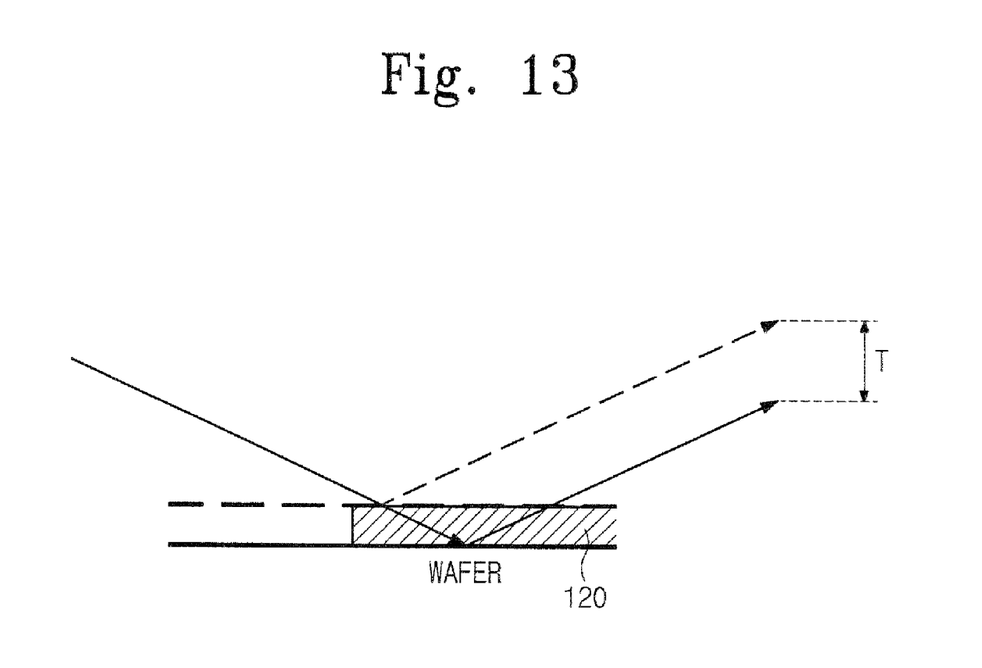
FIG. 13 is a cross-sectional view explaining a principle of sensing the change of a height of the detector in the sensor according to an exemplary embodiment of the present invention.
Figure 14:
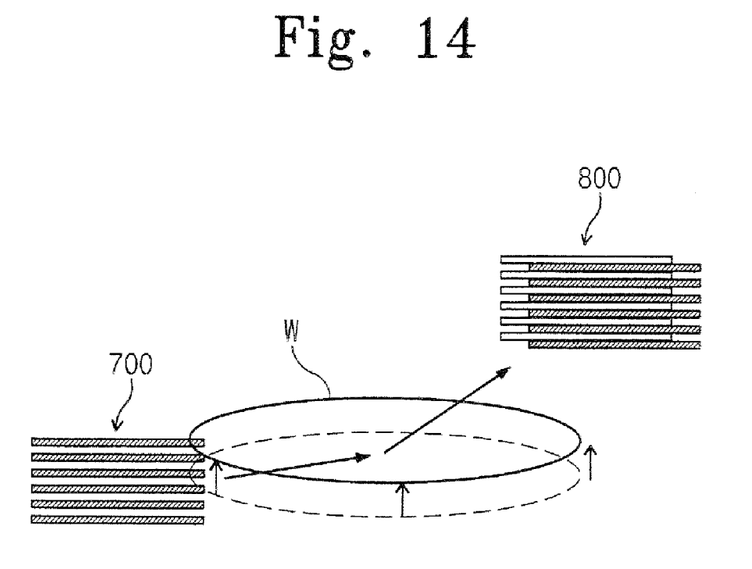
FIGS. 14 and 15 are perspective views illustrating an example of sensing the height change of the detector according to an exemplary embodiment of the present invention.
Figure 15:
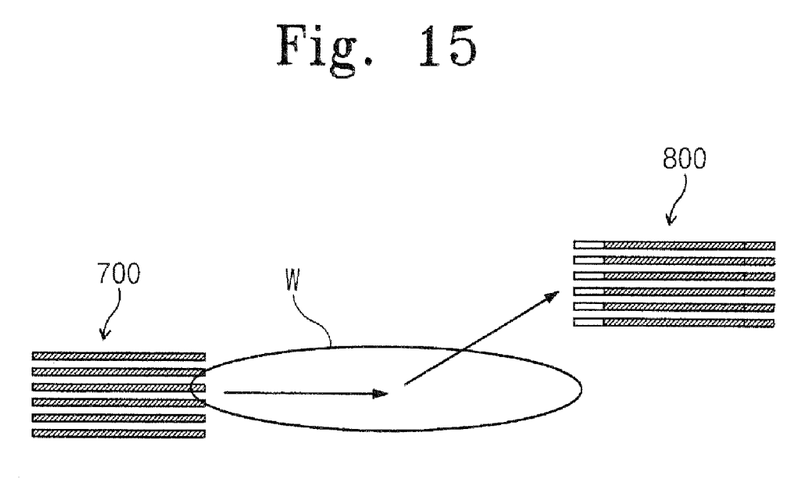

Referring to FIG. 13, whether the photoresist 120 is coated on the wafer (W) or not, the detector 800 detects the height change according to a path change of the laser beam reflected from the wafer (W). The height change (T) on the wafer (W), as shown in FIGS. 14 and 15, is represented as a position change of a slit shape of beam in the detection grating unit 832.

Figure 16:
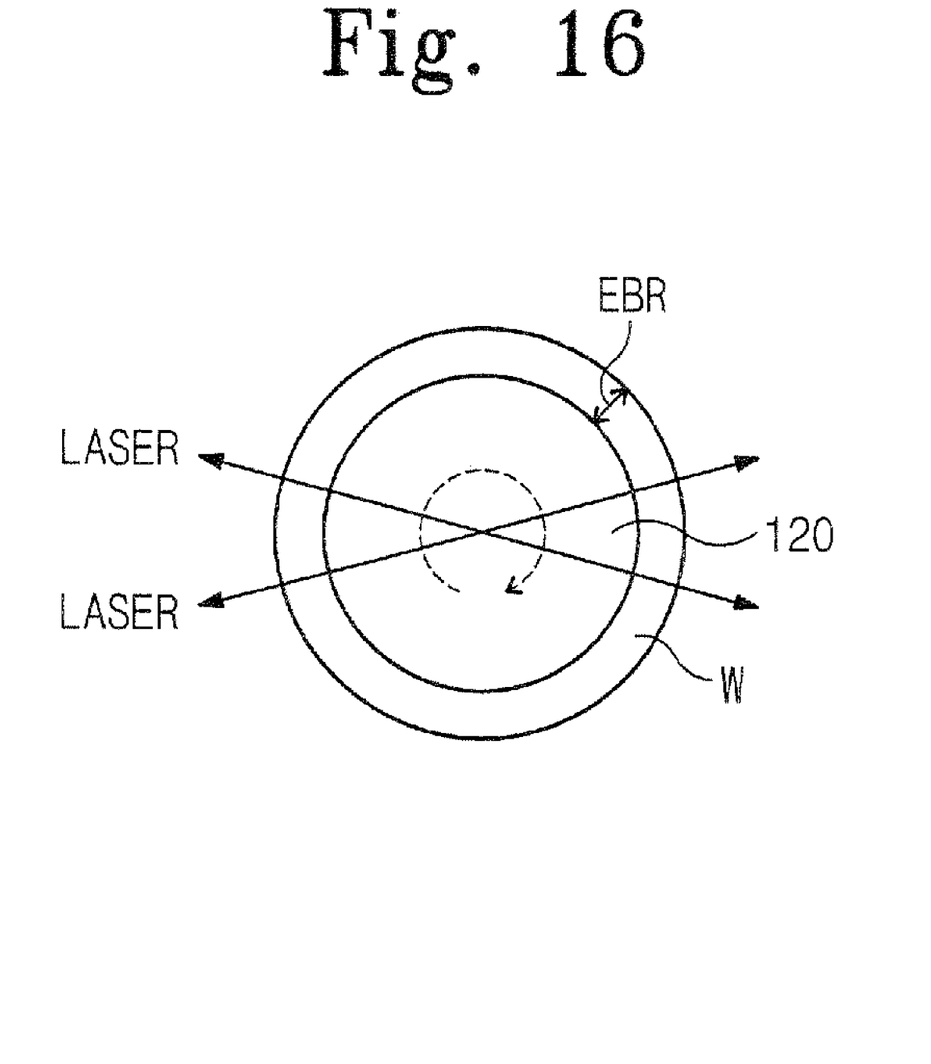
FIGS. 16 and 17 are plan views respectively illustrating a direction of the sensing operation of the sensor according to an exemplary embodiment of the present invention.
Figure 17:
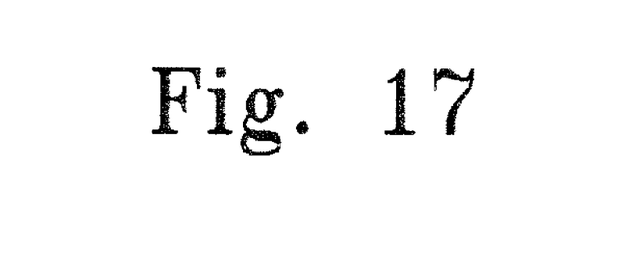
Figure 18:
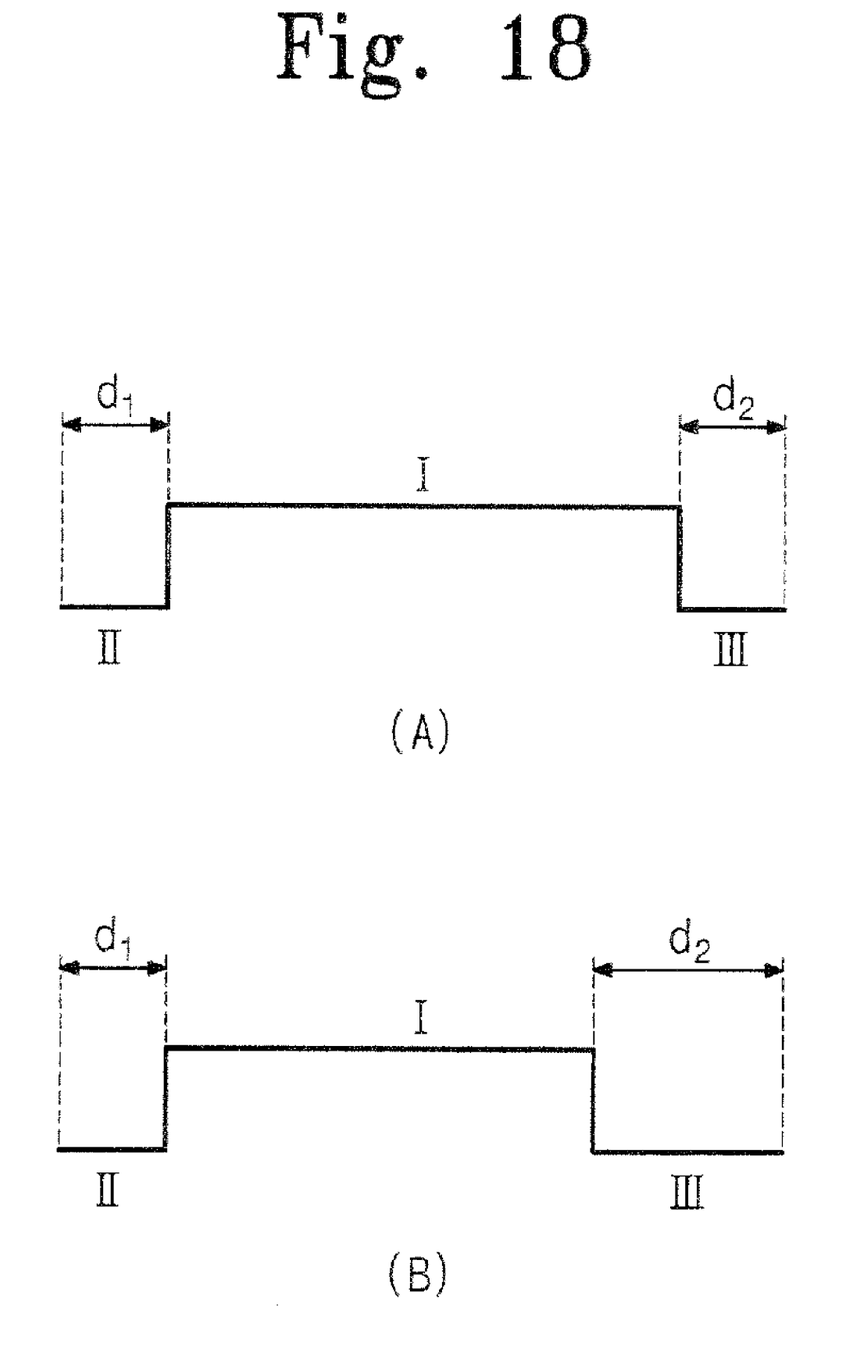
FIG. 18 is a graph visually illustrating result values of sensing according to an exemplary embodiment of the present invention.

Sensing units 100 and 900, as shown in FIGS. 1 and 9, may measure the wafer centering and the EBR size by crossing and sensing the whole surfaces of the wafer (W), as depicted in FIG. 16. On the other hand, as shown in FIG. 17, the sensing units 100 and 900 may measure the wafer centering and the EBR size by sensing only edges of the wafer (W) and enabling the wafer (W) to be rotated. As a result of sensing, as shown in FIG. 18, a part (I) having the photoresist on the wafer (W) and a part (II and III) not having the photoresist on the wafer (W) are sensed. If respective widths ($d_1$ and $d_2$) of the parts (II and III) are the same (A), the wafer centering is acceptable, and, if not so, the wafer centering is not acceptable.

Figure 19:
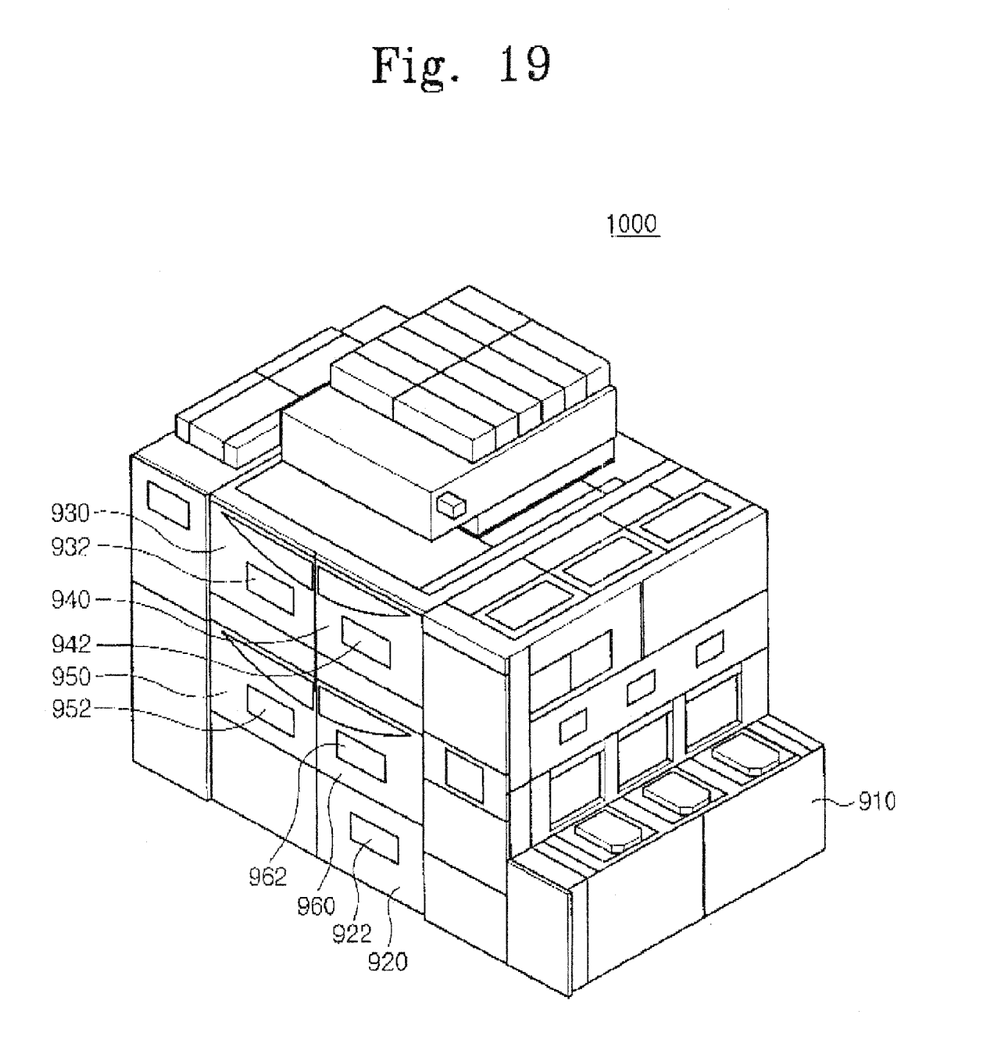
FIG. 19 shows a perspective view illustrating semiconductor equipment according to an exemplary embodiment of the present invention.

Referring to FIG. 19, the semiconductor manufacturing equipment 1000 includes a load port 910 on which a device configured to load the wafer such as a carrier is placed, a plurality of spinners 930, 940, 950, and 960, and a chemical control unit 920, where the spinner and control unit perform a desired processing. The spinners 930, 940, 950, and 960, respectively, include input/output boards 932, 942, 952, and 962, for inputting/outputting information on respective spinners 930, 940, 950, and 960. Likewise, the liquid control unit 920 includes the input/output board 922. At least one of the spinners 930, 940, 950, and 960, includes a coating process unit 200, and the sensing units 100 and 900 are installed in the coating process unit 200. The semiconductor manufacturing equipment 1000 is set at a regular interval, scans or transmits the laser beam onto the surface of the wafer (W) after finishing the process of the relevant unit 930, 940, 950, and 960, analyzes its waveform (see FIG. 18), and accordingly calculates the eccentricity of the wafer and an EBR size, respectively. As a result of performing feedback on the result data, if it is determined that the electricity of the wafer and the EBR size are of an acceptable magnitude, the semiconductor manufacturing equipment 1000 is normally operated, and, if not so, the operation of the semiconductor manufacturing equipment 1000 is stopped. Additionally, the wafer centering and the EBR size are automatically controlled by the main controller based on the result data.

As described above, the monitoring of the EBR size, according to the present invention, can be advanced, right after the EBR process, and the EBR size and the wafer centering can be automatically controlled using the feedback system. In case the EBR size is poor, it is capable of increasing the reliability of measurement of the EBR size and further the quality of the wafer.

It should be understood by those of ordinary skill in the art that various replacement, modifications and changes in the form and details may be made therein without departing from the sprit and scope of the present invention as defined by the following claims. Therefore, it is to be appreciated that the above described embodiments are for purpose of illustration only and are not to be construed as limitations of the invention.

What is claimed is:

1. A wafer processing method, comprising:
   providing a wafer;
   coating a predetermined material on the wafer;
   removing the predetermined coating material from an edge of the wafer;
   irradiating a laser beam onto the wafer edge from which the predetermined material is removed;
   obtaining information on a predetermined position of the wafer based on a sensing position of the laser beam reflected from the wafer edge; and
   correcting the position of the wafer, if the information indicates that the wafer is not in the predetermined position.

2. The processing method of claim 1, wherein the step of irradiating the laser beam on the wafer edge from which the predetermined material is removed and obtaining the information on the position of the wafer according to the sensing position of the laser beam reflected from the wafer edge comprises irradiating a laser beam crossing the upper part of the wafer.

3. The method of claim 1, wherein the step of irradiating the laser beam on the wafer edge from which the predetermined material is removed and obtaining the information on the position of the wafer according to the sensing position of the laser beam reflected from the wafer edge comprises rotating the wafer and irradiating the laser beam on an edge of the rotating wafer.

4. The method of claim 1, wherein the step of irradiating the laser beam on the wafer edge, from which the predetermined material is removed, and obtaining the information on the position of the wafer according to the sensing position of the laser beam reflected from the wafer edge further comprises measuring the width of the wafer edge from which the predetermined material is removed.

5. The method of claim 1, wherein the irradiated laser beam crosses an upper surface of the wafer.

6. The method of claim 1, wherein the laser beam is irradiated on an edge of the wafer.

7. The method of claim 6, wherein the laser beam is irradiated using a sensor.

8. The method of claim 7, wherein the sensor includes a projector.

9. The method of claim 7, wherein the sensor irradiates the laser beam on an edge of a rotating wafer.

10. The method of claim 1, wherein the wafer is supported on a rotatable device.

11. The method of claim 10, wherein the rotatable device comprises a rotatable chuck.

12. The method of claim 1, wherein the information regarding the predetermined position of the wafer includes at least one of the centering status of the wafer as supported on the rotatable device and the edge bead removal size of the wafer, respectively.

* * * * *